(12) United States Patent
Brusasco

(10) Patent No.: US 10,874,878 B2
(45) Date of Patent: Dec. 29, 2020

(54) PARTICLE THERAPY APPARATUS COMPRISING AN MRI

(71) Applicant: Ion Beam Applications S.A., Louvain-la-Neuve (BE)

(72) Inventor: Caterina Brusasco, Bossière (BE)

(73) Assignee: Ion Beam Applications S.A., Louvain-la-Neuve (BE)

( * ) Notice: Subject to any disclaimer, the term of this patent is extended or adjusted under 35 U.S.C. 154(b) by 484 days.

(21) Appl. No.: 15/727,544

(22) Filed: Oct. 6, 2017

(65) Prior Publication Data

US 2018/0099158 A1   Apr. 12, 2018

(30) Foreign Application Priority Data

Oct. 11, 2016   (EP) .................................... 16193327

(51) Int. Cl.
*A61N 5/10* (2006.01)
*G01R 33/3873* (2006.01)
*G01R 33/421* (2006.01)

(52) U.S. Cl.
CPC ......... *A61N 5/1049* (2013.01); *A61N 5/1043* (2013.01); *A61N 5/1081* (2013.01); *G01R 33/3873* (2013.01); *G01R 33/4215* (2013.01); *A61N 2005/1055* (2013.01); *A61N 2005/1087* (2013.01)

(58) Field of Classification Search
None
See application file for complete search history.

(56) References Cited

U.S. PATENT DOCUMENTS

| | | | |
|---|---|---|---|
| 4,694,836 | A | 9/1987 | Buikman et al. |
| 4,870,287 | A | 9/1989 | Cole et al. |
| 4,905,267 | A | 2/1990 | Miller et al. |
| 6,545,476 | B1 | 4/2003 | Heid |

(Continued)

FOREIGN PATENT DOCUMENTS

| | | |
|---|---|---|
| EP | 0 186 238 A2 | 7/1986 |
| EP | 0 635 849 A1 | 1/1995 |

(Continued)

OTHER PUBLICATIONS

Boye, Dirk, et al., "Mapping motion from 4D-MRI to 3D-CT for use in 4D dose calculations: A technical feasibility study," *Medical Physics*, vol. 40, No. 6, pp. 61702-1 to 61702-11 (May 7, 2013).

(Continued)

*Primary Examiner* — Katherine L Fernandez
(74) *Attorney, Agent, or Firm* — Finnegan, Henderson, Farabow, Garrett & Dunner LLP

(57) ABSTRACT

The present disclosure relates to a particle therapy apparatus for irradiating a target with a charged particle beam. In one implementation, the apparatus includes an isocentric gantry rotatable about an axis and configured to direct a particle beam towards an isocenter of gantry and according to a final beam direction, a magnetic resonance imaging system configured to generate a main magnetic field parallel to the final beam direction, and a passive magnetic shield surrounding the magnetic resonance imaging system, the passive magnetic shield and the magnetic resonance imaging system being synchronously rotatable with the gantry about the axis.

20 Claims, 2 Drawing Sheets

(56) References Cited

U.S. PATENT DOCUMENTS

| | | |
|---|---|---|
| 7,944,208 B2 | 5/2011 | Dutto et al. |
| 8,331,531 B2 | 12/2012 | Fahrig et al. |
| 8,410,730 B2 | 4/2013 | Abs |
| 8,427,148 B2 | 4/2013 | O'Connor |
| 2004/0199068 A1 | 10/2004 | Bucholz et al. |
| 2008/0071131 A1 | 3/2008 | Rietzel |
| 2010/0174172 A1 | 7/2010 | Ein-Gal |
| 2010/0239066 A1 | 9/2010 | Fahrig et al. |
| 2011/0156703 A1 | 6/2011 | O'Connor |
| 2011/0237859 A1* | 9/2011 | Kuhn .............. A61N 5/1031 600/1 |
| 2012/0160996 A1 | 6/2012 | Jongen |
| 2013/0147476 A1 | 6/2013 | Shvartsman et al. |
| 2013/0187060 A1* | 7/2013 | Jongen .............. A61N 5/10 250/396 R |
| 2014/0252227 A1 | 9/2014 | Sasai et al. |
| 2015/0217139 A1 | 8/2015 | Bert et al. |
| 2016/0011288 A1 | 1/2016 | Overweg et al. |

FOREIGN PATENT DOCUMENTS

| | | |
|---|---|---|
| EP | 2 196 241 A1 | 6/2010 |
| EP | 2 853 292 A1 | 4/2015 |
| EP | 2 977 083 A1 | 1/2016 |
| GB | 2507792 A | 5/2014 |
| KR | 10-2015-0049317 A | 5/2015 |
| KR | 10-2015-0060387 A | 6/2015 |
| KR | 2016 01 008119 A | 8/2016 |
| WO | WO 89/09906 | 10/1989 |
| WO | WO 03/092812 A1 | 11/2003 |
| WO | WO 2008/142695 A1 | 11/2008 |
| WO | WO 2009/067428 A1 | 5/2009 |
| WO | WO 2009/156896 A1 | 12/2009 |
| WO | WO 2010/067287 A1 | 6/2010 |
| WO | WO 2015/197475 | 12/2015 |

OTHER PUBLICATIONS

Richter, Christian, et al., "First clinical application of a prompt gamma based in vivo proton range verification system," *Radiotherapy and Oncology*, vol. 118, No. 2, pp. 232-237 (Jan. 13, 2016).

Assmann, W., et al., "Ionoacoustic characterization of the proton Bragg peak with submillimeter accuracy," *Medical Physics*, vol. 42, No. 2, pp. 567-574 (Jan. 9, 2015).

Wachowicz, K., et al., "Geometric distortion and shimming considerations in a rotating MR-linac design due to the influence of low-level external magnetic fields," *Medical Physics*, vol. 39, No. 5, pp. 2659-2668 (Apr. 19, 2012).

Pedroni, Eros, et al., "The PSI Gantry 2 : a second generation proton scanning gantry," *Zeitschrift für Medizinische Physik*, vol. 14, No. 1, pp. 25-34 (2004).

European Search Report issued in counterpart EP Application No. 16 19 3327 dated Apr. 12, 2017; 4 pages.

\* cited by examiner

PARTICLE THERAPY APPARATUS COMPRISING AN MRI

CROSS-REFERENCE TO RELATED APPLICATIONS

The application claims the benefit of priority to European Application No. 16193327.0, filed Oct. 11, 2016, the contents of which are incorporated herein by reference.

TECHNICAL FIELD

The present disclosure relates to an apparatus for irradiating a target with a charged particle beam for therapy purposes and comprising a magnetic resonance imaging (MRI) system for imaging the target.

BACKGROUND

Conventional particle therapy apparatuses may allow for irradiating a target volume of a patient with a beam of energetic charged particles, such as protons. While travelling through the patient, the charged particle beams generally lose energy, and the majority of the energy of the particle beam is generally deposited at the end of the beam path that is called the Bragg peak. This may allow an accurate delivery of high dose of energy in a target volume while minimizing the dose of energy delivered to surrounding tissues. The high dose of energy delivered may induce damages to the DNA of cells, killing them or stopping their reproduction. Charged particle therapy may therefore be used in the field of cancer treatment, as cancerous cells are particularly vulnerable to attacks on DNA.

One drawback of charged particle therapy is that even small movements of the patient, such as breathing movements, may lead to significant deviations of the delivered dose in the course of the irradiation of the target with the beam. Therefore, it may be desirable to use real-time imaging to track the target and to adapt the beam to the motion of organs and to the target. One of the real-time imaging systems that may be used is a magnetic resonance imaging (MRI) system.

A particle therapy apparatus comprising a MRI system is discussed, for example, in PCT publication No. WO 2015/197475. This document generally relates to a particle therapy apparatus including a conventional rotatable gantry that may comprise a plurality of bending magnets to bend and direct the particle beam towards the target (e.g., towards the isocentre) in a direction perpendicular to the axis of rotation of the gantry. The MRI system may be arranged such that the direction of its main magnetic field (Bo) is the same as the direction of the axis of rotation of the gantry, which may generally be chosen to be horizontal for the comfort of the patient, who may then be placed horizontally in the particle therapy apparatus.

European Pat. publication No. 2196241 generally relates to a particle therapy apparatus wherein the main magnetic field of the MRI system may be in the vertical direction and may be combined with a fixed beamline, wherein the beam may be entering the MRI system through an opening at the top of the MRI system. This arrangement may reduce the influence of the magnetic field of the MRI magnets on the path of charged particles. The subject support may be adapted for rotational motion during operation of the therapeutic apparatus.

US Pat. publication No. 2010/0239066 generally relates to a particles therapy apparatus that generates a treatment beam and a magnetic field disposed parallel to the treatment beam, wherein a target may be disposed along the treatment beam. The treatment beam may be a proton beam and the magnetic field may be from a MRI system. The magnetic field may operate in coordination with operation of the treatment beam and may narrow said beam. The apparatus generating both said treatment beam and said magnetic field may be configured to rotate with respect to said target. Accordingly, this document generally relates to an inline design approach.

Nevertheless, there is still a need for improvement of the performances of particle therapy apparatus comprising a real time imaging system. For example, there is a need for further narrowing the particle beam in order to have a more precise delivery of high dose of energy in the target volume. There is also a need for an efficient apparatus integrating a particle therapy apparatus and a MRI system that is more compact.

Embodiments of the present disclosure may provide a compact solution to at least one of the drawbacks discussed above.

SUMMARY

According to a first aspect, the present disclosure relates to a particle therapy apparatus for irradiating a target with a charged particle beam. The apparatus may comprise:
 a particle accelerator to generate the charged particle beam;
 an isocentric gantry configured to rotate about an axis Y and comprising a plurality of bending magnets arranged along a beam path, said plurality of magnets comprising a first bending magnet and a last bending magnet, the first bending magnet being configured to receive the particle beam along the axis Y and to bend and direct the particle beam away from the axis Y, the last bending magnet being configured to bend and direct the particle beam towards the isocentre of the gantry and according to a final beam direction; and
 a magnetic resonance imaging system comprising a first and a second main magnet unit separated by a free air gap and arranged respectively on opposites sides of the gantry's isocentre, the first main magnet unit being the one closest to the last bending magnet of the gantry, said first and second main magnet units being configured to generate together a main magnetic field (Bo) which is parallel to the final beam direction at the gantry's isocentre,
wherein the apparatus may further comprise a passive magnetic shield surrounding the first and second main magnet units of the magnetic resonance imaging system such that a part of the passive magnetic shield may be arranged between the last bending magnet of the gantry and the first main magnet unit of the magnetic resonance imaging system, wherein the said part of the passive magnetic shield may comprise a first through-hole defining a passageway through which the particle beam may pass to reach the gantry's isocentre, and further wherein the passive magnetic shield as well as the first and the second main magnet units of the magnetic resonance imaging system may all be synchronously rotatable with the gantry about the axis Y.

In some embodiments:
 The final beam direction may be a direction perpendicular to the axis Y;
 The first and second main magnet units of the MRI system and/or the passive magnetic shield may be fixed to the gantry so as to rotate synchronously with the gantry when the gantry is put into rotation;

The apparatus may further comprise at least one scanning magnet arranged on the gantry along the beam path—e.g., between the first and the last bending magnet of the gantry—and configured to scan the particle beam over the target;

The particle beam may be a beam of charged particles chosen among protons or ions;

The particle accelerator may be a cyclotron or a synchrotron;

Each of the first and second main magnet units of the magnetic resonance imaging system may comprise a superconducting electromagnet; and/or The isocentre of the gantry may coincide with the imaging centre of the magnetic resonance imaging system.

In some embodiments:

The passive magnetic shield may be configured to be unsaturated by the magnetic fields of the magnetic resonance imaging system and/or by the magnetic fields of the magnets of the gantry (bending magnets and/or scanning magnets);

The passive magnetic shield may be configured to be unsaturated by the magnetic fields of the magnetic resonance imaging system and/or by the fields of both the scanning magnets and the bending magnets of the gantry;

The passive magnetic shield may comprise a second through-hole facing the first through-hole along the final beam direction;

The passive magnetic shield may comprise a third through-hole whose axis may be parallel to or coincide with the axis Y and which may be dimensioned to allow a passage of a patient through it;

The passive magnetic shield may comprise a fourth through-hole facing the third through-hole along the Y axis;

The passive magnetic shield may comprise at least one yoke of ferromagnetic material;

The said yoke may have a parallelepiped shape; and/or

The first through-hole may have a diameter in the range of 10 cm to 50 cm.

According to a second aspect, the present disclosure relates to the use of a passive magnetic shield in a therapy apparatus for irradiating a target with a charged particle beam. The apparatus may comprise:

a particle accelerator to generate the charged particle beam;

an isocentric gantry configured to rotate about an axis Y and comprising a plurality of bending magnets arranged along a beam path, said plurality of magnets comprising a first bending magnet and a last bending magnet, the first bending magnet being configured to receive the particle beam along the axis Y and to bend and direct the particle beam away from the axis Y, the last bending magnet being configured to bend and direct the particle beam towards the isocentre of the gantry and according to a final beam direction; and a magnetic resonance imaging system comprising a first and a second main magnet units separated by a free air gap and arranged respectively on opposites sides of the gantry's isocentre, the first main magnet unit being the one closest to the last bending magnet of the gantry, said first and second main magnet units being configured to generate together a main magnetic field (Bo) which is parallel to the final beam direction at the gantry's isocentre, wherein the passive magnetic shield may be configured to surround the first and second main magnet units of the magnetic resonance imaging system such that part of the passive magnetic shield may be arranged between the last bending magnet of the gantry and the first main magnet unit of the magnetic resonance imaging system, wherein the said part of the passive magnetic shield may comprise a first through-hole defining a passageway through which the particle beam may pass to reach the gantry's isocentre, and further wherein the use may comprise having the passive magnetic shield as well as the first and second main magnet units of the magnetic resonance imaging system all be synchronously rotatable with the gantry about the axis Y.

The apparatus and use according to some embodiments of the present disclosure may provide a more compact solution to the above-noted problems.

BRIEF DESCRIPTION OF THE FIGURES

The figures are neither drawn to scale nor proportioned. Generally, similar or identical components are denoted by the same reference numerals in the figures.

DETAILED DESCRIPTION

For the purpose of the disclosure, the terms "comprising," "comprises" and "comprised of" as used herein are synonymous with "including," "includes," "containing" or "contains" and are inclusive and/or open-ended and do not exclude additional, non-recited members, elements or method steps. The terms "comprising," "comprises" and "comprised of" also include the term "consisting of."

The recitation of numerical ranges by endpoints includes all numbers and fractions subsumed within the respective ranges, as well as the recited endpoints.

The particular features, structures, characteristics or embodiments may be combined in any suitable manner, as would be apparent to a person skilled in the art from this disclosure, in one or more embodiments.

A particle therapy apparatus for irradiating a target with a charged particle beam for therapy purposes generally comprises a particle accelerator to generate the charged particle beam, a beam transport system to transport the particle beam from the particle accelerator to the target to be irradiated, and various other subsystems, for example, to shape the beam and/or to modify its energy and/or its intensity for the particular therapy envisaged. The target may, for example, be a diseased part, such as a tumor, in a patient's body. Hence, the term "target" used hereinafter may refer to such a tumor in addition to or in alternative to the patient himself.

Figure 1:
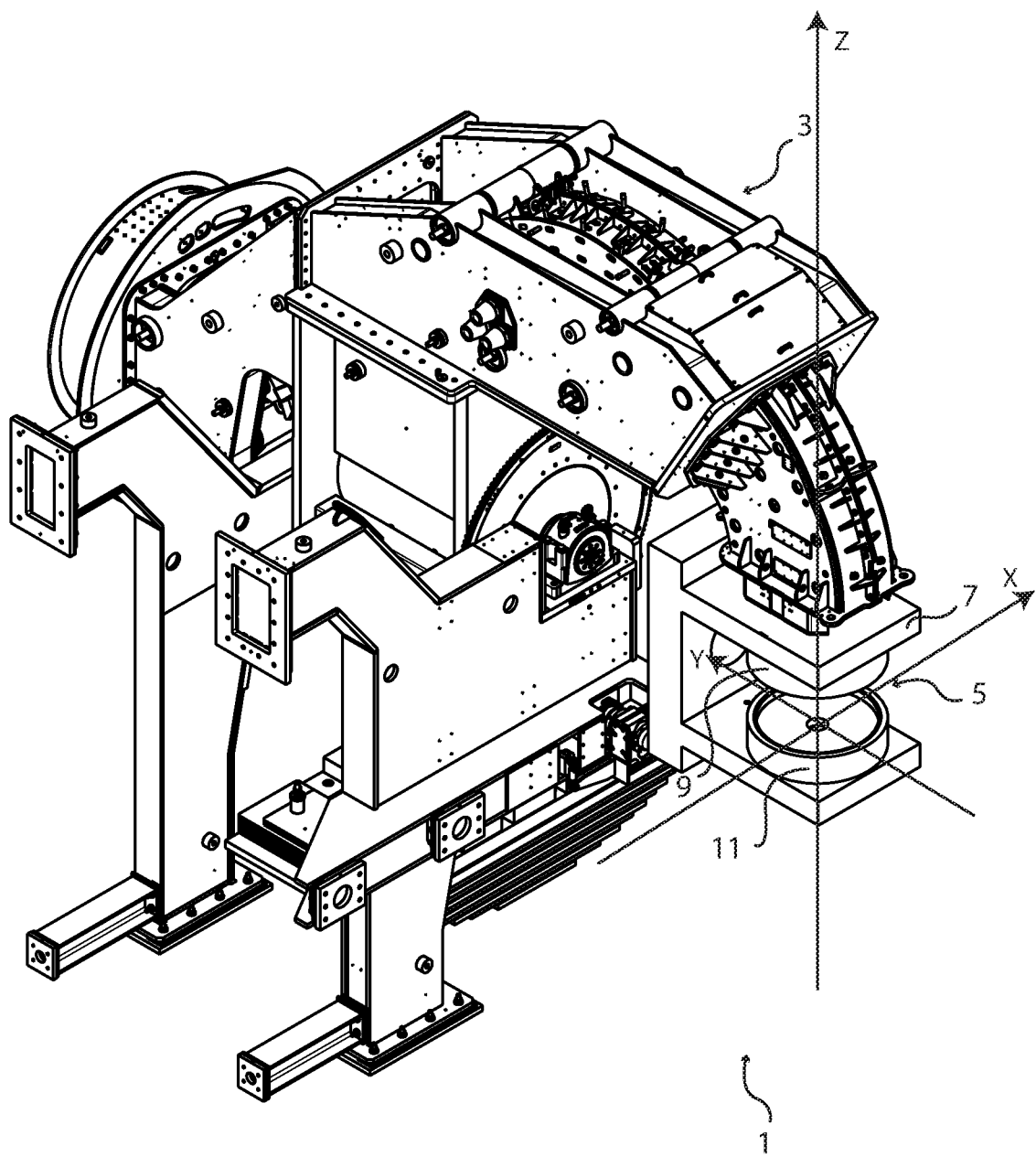
FIG. 1 is a view of a part of an apparatus of an example embodiment of the present disclosure.

Reference is now made to FIG. 1, which shows a part of a particle therapy apparatus 1 according to an example embodiment of the present disclosure. Particle therapy apparatus 1 may comprise a particle accelerator (not shown for the sake of clarity) to generate the charged particle beam, an isocentric gantry 3, which may be rotatable about an axis Y (e.g., in the shown orthogonal XYZ referential), and a part of a beam transport system (also not shown for the sake of clarity) to transport the particle beam, from where it is extracted from the particle accelerator to an entry point of the particle beam into a gantry beam line. In the example of FIG. 1, the particle beam enters the gantry beam line in parallel to or coincident with the rotation axis Y of the gantry. The rotatable gantry 3 may be isocentric because the particle beams exiting from the last bending magnet may, for any angle of rotation of the gantry, cross at a same point called the "isocentre," hereinafter sometimes referred to as the isocentre of the gantry. In some embodiments, due to the heavy weight and mechanical imperfections of the system, the isocentre may not be a single point but rather be a small sphere. In the example of FIG. 1, the isocentre is the origin of the XYZ referential.

In some embodiments, the gantry 3 may be rotatable over an angular range of at least 180° or over an angular range up to 360°.

The rotatable gantry 3 may comprise and/or support a plurality of bending magnets arranged in sequence along a beam path and including a first bending magnet and a last bending magnet. The first bending magnet of said sequence may be configured to receive the particle beam along the axis Y and to bend and direct the particle beam away from the axis Y. The last bending magnet of said sequence may be configured to bend and direct the particle beam towards the isocentre. The said sequence may comprise one or more additional bending magnets arranged on the gantry along the beam path between the first bending magnet and the last bending magnet.

According to some embodiments, the apparatus may further comprise a magnetic resonance imaging system 5 including a first main magnet unit 9 and a second main magnet unit 11. The first and second main magnet units may be separated by a free air gap and arranged respectively on opposite sides of the gantry's isocentre. In certain aspects, the first and second main magnet units may be arranged symmetrically with respect to the gantry's isocentre. The first main magnet unit 9 may be the one located closest to the last bending magnet of the gantry 3. The first main magnet unit 9 and second main magnet unit 11 may be arranged and configured to generate, together, a main magnetic field (Bo) parallel to the final beam direction at the gantry's isocentre, as depicted in FIG. 2.

According to some embodiments, the apparatus may further comprise a passive magnetic shield 7 surrounding the first main magnet unit 9 and second main magnet unit 11 of the magnetic resonance imaging system.

Figure 2:
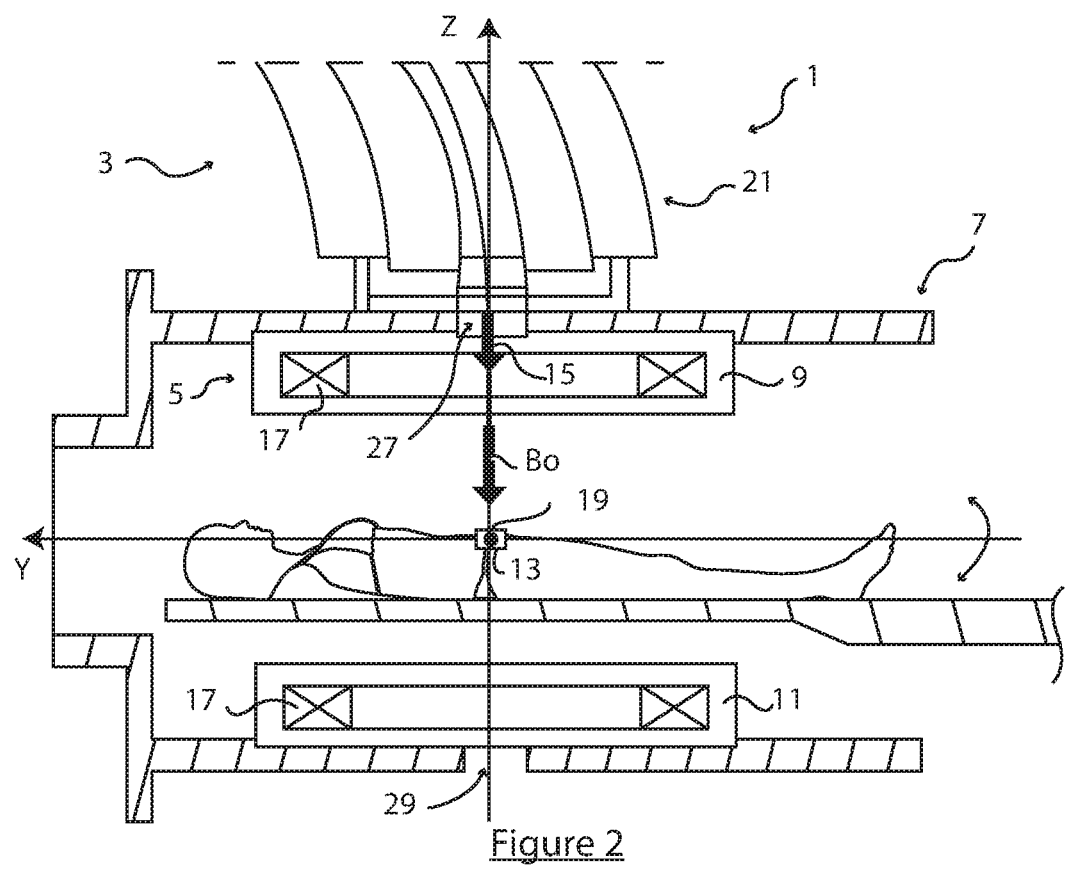
FIG. 2 is a cross sectional view of a part of the apparatus of FIG. 1.

Reference is now made to FIG. 2, which depicts a partial cross-sectional view of the apparatus of FIG. 1. FIG. 2 shows a part of the last bending magnet 21 of the gantry 3 of the apparatus 1. As depicted, the last bending magnet 21 may be configured to bend and direct the particle beam 15 towards the isocentre 19 of the gantry and according to a final beam direction. In this example, the final beam direction may be a direction perpendicular to the axis Y, regardless of the rotation angle of the gantry. In another embodiment (not illustrated), the last bending magnet of the gantry may be configured to bend and direct the particle beam 15 towards the isocentre 19 of the gantry and according to a final beam direction, which may form an angle alpha with the axis Y, such that alpha is larger than 70 degrees and smaller than 90 degrees, (or, e.g., larger than 80 degrees and smaller than 90 degrees), regardless of the rotation angle of the gantry.

The MRI system 5 may comprise a first main magnet unit 9 and a second main magnet unit 11 separated by an air gap and arranged respectively on opposite sides of the gantry's isocentre 19. Each of the first main magnet unit 9 and the second main magnet unit 11 may comprise a magnet 17, e.g., an electromagnet or a superconducting electromagnet, which, when excited, may generate, together, the main magnetic field Bo. As shown in FIG. 2, the first main magnet unit 9 and the second main magnet unit 11 may be arranged and configured to generate, together, a main magnetic field Bo parallel to the final beam direction at the gantry's isocentre and in the close vicinity thereof. Such main magnet units may have the general shape of an open torus. As shown in FIG. 2, the two tori may be arranged in such a way that their axes of revolution are both parallel to the final beam direction. In certain aspects, their axes of revolution may be identical. In some embodiments, the first main magnet unit 9 and the second main magnet unit 11 may be arranged such that they are not in the way of the path of the particle beam.

In some embodiments, the first main magnet unit 9 and the second main magnet unit 11 of the MRI system may be further arranged such that the imaging center of the MRI system coincides with isocentre 19 of the gantry 3. MRI images of the target 13 may then be taken at the isocentre. Such images may, for example, be used to track the position of the target in real time before, while, and/or after irradiating the target with the particle beam, and possibly to correct the beam path and/or the beam energy and/or the beam intensity in function thereof.

In one embodiment, the particle therapy apparatus may further comprise at least one scanning magnet (not depicted) arranged along the beam path and configured to scan the particle beam over the target. Such scanning magnets may be used, for example, in pencil beam scanning techniques (PBS), and will not be described in greater detail. In certain aspects, at least one such scanning magnet may be arranged on the gantry between the first and the last bending magnet 21.

In some embodiments, the apparatus 1 may further comprise a passive magnetic shield 7 surrounding the first main magnet unit 9 and the second main magnet unit 11 of the magnetic resonance imaging system 5, the first main magnet unit 9 being the one closest to the last bending magnet 21 of the gantry 3, as shown in FIG. 2. At least a part of the passive magnetic shield may be arranged between the last bending magnet 21 of the gantry 3 and the first main magnet unit 9 of the MRI system 5. Said part of the passive magnetic shield may comprise a first through-hole 27 defining a passageway through which the particle beam 15 may pass to reach the gantry's isocentre 19. In certain aspects, said first through-hole 27 may have a diameter ranging from 10 cm to 50 cm, e.g., ranging from 20 cm to 40 cm.

In one embodiment, the passive magnetic shield 7 may comprise at least one yoke of ferromagnetic material, such as iron, nickel, cobalt, their alloys (for example, the mu-metal), or the like. In one embodiment, the passive magnetic shield 7 may comprise one yoke. In another embodiment, the passive magnetic shield 7 may comprise two or more yokes, which may be concentric and/or nested.

In some embodiments, the yoke 7 may have a parallel-epiped shape, e.g., a rectangular parallelepiped shape. In the embodiment illustrated in FIGS. 1 and 2, the yoke 7 has a rectangular parallelepiped shape and three faces: a superior base comprising the first through-hole 27 and an inferior base, which are both parallel to the Y axis, and one lateral face which is perpendicular to the Y axis and is located at the left side of the isocentre (e.g., at the side of the gantry entry point). Such a "laying U" configuration may have an efficient passive magnetic shielding.

Figure 3:
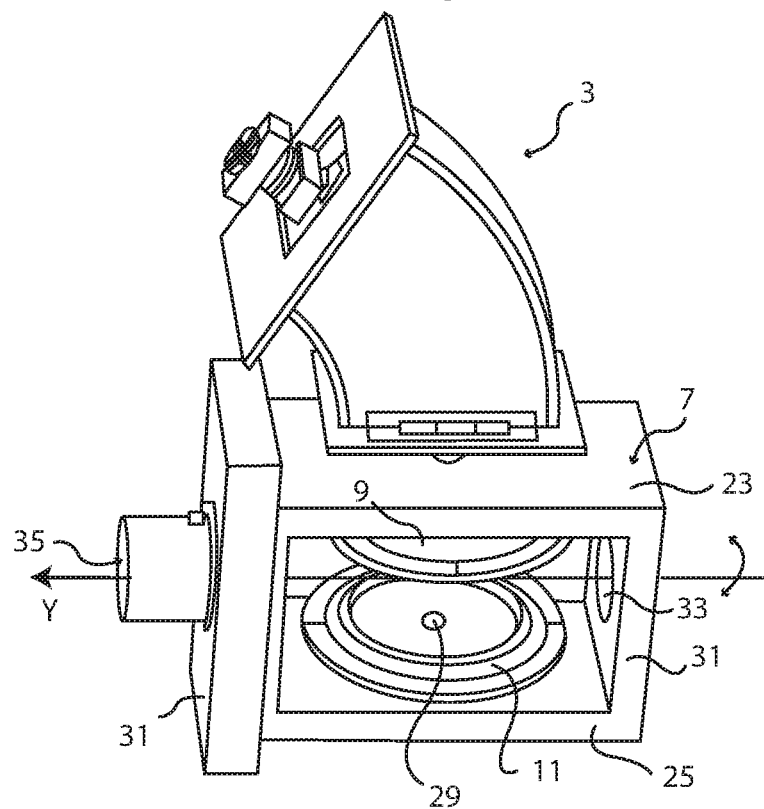
FIG. 3 is a perspective view of a part of an apparatus according to an example embodiment of the present disclosure.

In one embodiment, as illustrated in FIG. 3, the yoke may have four faces: a superior base 23 and an inferior base 25, which are both parallel to the Y axis, and two lateral faces 31, which are both perpendicular to said Y axis. The superior base 23 may be located between the last bending magnet 21 of the gantry 3 and the first main magnet 9 of the MRI system. Said superior base 23 may comprise the first through-hole through which the particle beam may pass to reach the gantry's isocentre.

Thus, referring to FIGS. 2 and 3, the yoke 7 may have an open configuration, wherein one, two or three of its lateral faces are open. Such a laterally opened configuration may be sufficient to allow the yoke to be used as passive magnetic shield while allowing the yoke to be lighter in weight and/or more comfortable and/or less stressful for patients, e.g., those suffering from claustrophobia.

In one embodiment, the passive magnetic shield 7 may further comprise a second through-hole 29 facing the first through-hole 27 along the final beam direction. For example, the second through-hole 29 may have same diameter as the first through-hole 27. In the embodiments of FIGS. 2 and 3, the second through-hole may be a hole in the inferior base of the magnetic shield. This second through-hole may allow for further imaging of the target from a point of view located under the said inferior base.

In the embodiment of FIG. 3, the passive magnetic shield 7 may further comprise a third through-hole 33 whose axis may coincide with the axis Y and which may be dimensioned to allow a passage of a patient through it. In some embodiments, the passive magnetic shield 7 may comprise a fourth through-hole 35 facing the third through-hole 33 along the Y axis. In the embodiment of FIG. 3, the third through-hole 33 and the fourth through-hole 35 are located respectively on the two lateral faces 31 of the yoke and are coaxial with the Y axis.

In some embodiments, at least one lateral face of the yoke may be higher in size that the external distance between the two bases.

The passive magnetic shield 7 may be designed and dimensioned to be unsaturated by the magnetic fields generated by the MRI system and/or to be unsaturated by the magnetic fields generated by the magnetic elements of the gantry, such as the bending magnets and/or the scanning magnets, for example.

According to some embodiments, the passive magnetic shield 7, as well as the first main magnet unit 9 and the second main magnet unit 11 of the MRI system 5, may all be synchronously rotatable about the axis Y with the gantry 3. In other words, the passive magnetic shield 7, as well as the first main magnet unit 9 and the second main magnet unit 11 of the MRI system 5, may all be rotatable about the axis Y at the same rotational speed and with the same phase as the gantry 3. This may be achieved in several ways. One way may be to use three motors: a first motor for rotating the gantry, a second motor for rotating the magnetic shield and a third motor for rotating the first and second main magnet units of the MRI system. The three motors may then be synchronized. Alternatively, two motor may be used: a first motor for rotating the gantry and a second motor for rotating both the magnetic shield and the first and second main magnet units of the MRI system together, which may be realized by attaching together the magnetic shield and the first and second main magnet units of the MRI system. The two motors may then be synchronized. Alternatively, a single motor may be used for rotating together the gantry 3, the magnetic shield 7, and the first main magnet unit 9 and the second main magnet unit 11 of the MRI system, which may be realized by attaching these subsystems together and by operatively connecting at least one of them to the motor.

In one embodiment, the first main magnet unit 9 and the second main magnet unit 11 may be fixed to the passive magnetic shield 7, and/or the passive magnetic shield 7 may be fixed to the gantry 3, such that there is no relative movement between the gantry 3, the passive magnetic shield 7 and/or the two main magnet units of the MRI system 5. In such an example, a single motor may be provided to rotate these three subsystems together. For example, this single motor may be operatively connected to the gantry.

Rollers may also be provided in order to sustain the passive magnetic shield, which is generally quite heavy.

In some embodiments, the particle beam may be a beam of electrically charged particles, excluding electrons. For example, the particle beam may be a beam of protons or a beam of carbon ions. In some embodiments, the particle accelerator may be a cyclotron, a synchrotron, a synchrocyclotron (e.g., a superconducting synchrocyclotron), or the like. In some embodiments, the particle accelerator may be configured to generate and deliver a beam of charged particles whose energy is higher than 60 MeV.

Embodiments of the present disclosure may allow for lowering the magnetic interaction and/or the perturbation between the MRI and particle treatment subsystems, such that the particle therapy apparatus may show improved performances and/or may be made more compact.

The invention claimed is:
1. A particle therapy apparatus for irradiating a target with a charged particle beam, comprising:
   a particle accelerator configured to generate the charged particle beam;
   a gantry having an isocenter rotatable about an axis, the gantry including:
      a plurality of bending magnets arranged along a beam path and having a first bending magnet and a last bending magnet,
      the first bending magnet configured to receive the charged particle beam along the axis and to bend and direct the charged particle beam away from the axis,
      the last bending magnet configured to bend and direct the charged particle beam towards the isocenter and according to a final beam direction;
   a magnetic resonance imaging system including:
      a first main magnet unit and a second main magnet unit arranged respectively on opposite sides of the isocenter,
      the first main magnet unit being closer to the last bending magnet than the second main magnet unit,
      the first main magnet unit and the second main magnet unit configured to generate a main magnetic field parallel to the final beam direction at the isocenter; and
   a passive magnetic shield surrounding the first main magnet unit and the second main magnet unit, the passive magnetic shield having an upper portion arranged between the last bending magnet and the first main magnet unit, and a lower portion opposite the upper portion,
   wherein the upper portion of the passive magnetic shield includes a first through-hole defining a passageway through which the charged particle beam passes to reach the isocenter,
   wherein the lower portion of the passive magnetic shield borders a lower surface of the second main magnet unit, and
   wherein the first main magnet unit, the second main magnet unit, and the passive magnetic shield are all synchronously rotatable with the gantry about the axis.
2. The particle therapy apparatus of claim 1, wherein the final beam direction is perpendicular to the axis.

3. The particle therapy apparatus of claim 1, wherein the first main magnet unit and the second main magnet unit are both fixedly connected to the passive magnetic shield.

4. The particle therapy apparatus of claim 1, wherein the passive magnetic shield is fixedly connected to the gantry.

5. The particle therapy apparatus of claim 1, wherein the passive magnetic shield is configured to be unsaturated by magnetic fields of the magnetic resonance imaging system.

6. The particle therapy apparatus of claim 1, wherein the passive magnetic shield is configured to be unsaturated by magnetic fields of the gantry.

7. The particle therapy apparatus of claim 1, further comprising at least one scanning magnet arranged along the beam path and configured to scan the charged particle beam over the target.

8. The particle therapy apparatus of claim 7, wherein the at least one scanning magnet is arranged between the first bending magnet and the last bending magnet.

9. The particle therapy apparatus of claim 1, wherein the lower portion of the passive magnetic shield further includes a second through-hole defining a passageway for imaging the target, the second through-hole facing the first through-hole along the final beam direction.

10. The particle therapy apparatus of claim 9, wherein the passive magnetic shield further includes a third through-hole having a second axis parallel to or coincident with the axis and being dimensioned to allow passage of a patient.

11. The particle therapy apparatus of claim 1, wherein the passive magnetic shield further includes at least one yoke.

12. The particle therapy apparatus of claim 11, wherein the at least one yoke is ferromagnetic.

13. The particle therapy apparatus of claim 11, wherein the at least one yoke has a parallelepiped shape.

14. The particle therapy apparatus of claim 1, wherein the first through-hole has a diameter between 10 cm and 50 cm.

15. The particle therapy apparatus of claim 14, wherein the first through-hole has a diameter between 20 cm and 40 cm.

16. The particle therapy apparatus of claim 1, wherein the charged particle beam is free of electrons.

17. The particle therapy apparatus of claim 16, wherein the charged particle beam is a beam of at least one of protons or ions.

18. The particle therapy apparatus of claim 1, wherein the particle accelerator is at least one of a cyclotron or a synchrotron.

19. The particle therapy apparatus of claim 1, wherein each of the first main magnet unit and the second main magnet unit is a superconducting electromagnet.

20. The particle therapy apparatus of claim 1, wherein the isocenter coincides with an imaging center of the magnetic resonance imaging system.

* * * * *